United States Patent
Hari et al.

(10) Patent No.: US 10,668,045 B2
(45) Date of Patent: Jun. 2, 2020

(54) TOPICAL MASSAGE OIL AND CREAM CONTAINING CBD, CBN, CURCUMIN AND BOSWELLIA RESIN

(71) Applicant: Bright Green Corporation, Wilmington, DE (US)

(72) Inventors: V. Hari, Orlando, FL (US); John Stockwell, Leamington (CA)

(*) Notice: Subject to any disclaimer, the term of this patent is extended or adjusted under 35 U.S.C. 154(b) by 0 days.

(21) Appl. No.: 16/510,233

(22) Filed: Jul. 12, 2019

(65) Prior Publication Data

US 2020/0016115 A1 Jan. 16, 2020

Related U.S. Application Data

(60) Provisional application No. 62/696,931, filed on Jul. 12, 2018.

(51) Int. Cl.

| | | |
|---|---|---|
| *A61K 31/05* | (2006.01) | |
| *A61K 31/185* | (2006.01) | |
| *A61K 31/352* | (2006.01) | |
| *A61K 9/00* | (2006.01) | |
| *A61K 31/19* | (2006.01) | |
| *A61K 31/12* | (2006.01) | |

(52) U.S. Cl.
CPC .......... *A61K 31/352* (2013.01); *A61K 9/0014* (2013.01); *A61K 31/05* (2013.01); *A61K 31/12* (2013.01); *A61K 31/19* (2013.01)

(58) Field of Classification Search
CPC .............................. A61K 31/05; A61K 31/185
USPC .................................................. 514/557, 733
See application file for complete search history.

(56) References Cited

U.S. PATENT DOCUMENTS

| | | | | |
|---|---|---|---|---|
| 2016/0256410 | A1* | 9/2016 | Aung-Din | A61K 9/0017 |
| 2018/0311184 | A1* | 11/2018 | Hoag | A61K 31/618 |
| 2018/0369192 | A1* | 12/2018 | Green | A61K 36/185 |
| 2019/0275095 | A1* | 9/2019 | Spencer | A61K 47/44 |

FOREIGN PATENT DOCUMENTS

| | | | | |
|---|---|---|---|---|
| EP | 2444081 A1 * | 4/2012 | | A61K 31/19 |
| WO | WO-2017160923 A1 * | 9/2017 | | A61K 9/0014 |

* cited by examiner

*Primary Examiner* — Raymond J Henley, III
(74) *Attorney, Agent, or Firm* — Carlson, Gaskey & Olds, P.C.

(57) ABSTRACT

An example method of treating a medical issue includes applying a composition to a skin area corresponding to a location afflicted with the medical issue. The composition includes a blend of Cannabidiol (CBD) oil and Cannabinol (CBN) oil fortified with curcumin from turmeric, Boswellic acid, and polycyclic terpenes from *Boswellia serrata*. The medical issue includes at least one of osteoarthritis, joint pain associated with natural causes or injury, reduced joint function and flexibility after injury or other causes, and photo-aging. A composition including a blend of pure CBD oil and CBN oil fortified with curcumin from turmeric and Boswellic acid along with polycyclic terpenes from *Boswellia serrata* is also disclosed.

20 Claims, No Drawings

TOPICAL MASSAGE OIL AND CREAM CONTAINING CBD, CBN, CURCUMIN AND BOSWELLIA RESIN

CROSS-REFERENCE TO RELATED APPLICATIONS

This application claims priority to U.S. Provisional Application No. 62/696,931, which was filed on Jul. 12, 2018, and is incorporated herein by reference.

BACKGROUND

The present disclosure relates to a topical treatment for medical issues, and more particularly to an oil or cream for addressing osteoarthritis, joint pain, and/or the protection or restoration of skin health.

Osteoarthritis, joint pain, and photo-aging are common ailments for which those afflicted desire treatment.

SUMMARY

An example method of treating a medical issue includes applying a composition to a skin area corresponding to a location afflicted with the medical issue. The composition includes a blend of Cannabidiol (CBD) oil and Cannabinol (CBN) oil fortified with curcumin from turmeric, Boswellic acid, and polycyclic terpenes from *Boswellia serrata*. The medical issue includes at least one of osteoarthritis, joint pain associated with natural causes or injury, reduced joint function and flexibility after injury or other causes, and photo-aging.

An example method of treating a medical issue includes applying a composition as a face cream, the composition including a blend of CBD oil and CBN oil fortified with curcumin from turmeric, Boswellic acid, and polycyclic terpenes from *Boswellia serrata*.

An example composition includes a blend of pure CBD oil and CBN oil fortified with curcumin from turmeric and Boswellic acid along with polycyclic terpenes from *Boswellia serrata*.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

The present disclosure describes an anti-inflammatory, healing topical oil-cream and massage formulation for treating pain and inflammation associated with osteoarthritis and joint pain due to natural causes or injury, and restoring flexibility of the joints, as well as healing and protection or restoration of skin health. This formulation is made of a non-psychoactive chromatographically purified CBD and CBN oil base, mixed with curcumin containing turmeric oil and resin from *Boswellia serrata*. This anti-inflammatory, tissue restorative oil or cream can be massaged or rubbed on the affected areas every day for reducing inflammation and restoring joint mobility as well as improving skin health.

The CBD and CBN from oil extracts of *Cannabis sativa* and its various subspecies, varieties, hybrids, bio-eco types have anti-inflammatory and pain relieving properties. Likewise, turmeric oil extracts from *Curcuma longa* containing Curcuminoids have anti-inflammatory properties as well as immune modulatory functions. *Boswellia serrata*, also known as Indian frankincense, exudes a resin containing Boswellic acid and polycyclic terpenes, which have pain relieving, anti-inflammatory and skin anti-aging properties.

According to one example embodiment, the CBD and CBN are extracted using a process that includes preparing medicinally important fresh plants by washing, cleaning and disinfecting the plants. In some examples, UV radiation disinfects the plants. Other examples include Ozonolysis for disinfecting. Once cleaned and disinfected, extraneous materials and microorganisms are removed from the plant material.

The fresh plants are then chopped into pieces, bagged and frozen at approximately −80° C. The frozen pieces are subsequently powdered or pulverized in the presence of dry ice (e.g., frozen $CO_2$). In some examples, the plant pieces are dried and then pulverized and powdered.

The powdered material is then suspended in an aqueous buffer containing approximately 1 mg/ml of pectinases, cellulases and proteases, vacuum infiltrated and incubated at approximately 37° C. for 1-24 hours, depending on the amount of plant material being extracted. Containers of the suspended plant material can be placed on a shaker platform and are gently shaken to distribute the contents, thereby allowing the plant cell walls and membranes to be digested, and releasing the contents into the aqueous media.

The contents of the containers are heated, such as by steam heat, to evaporate the aqueous phase, leaving the solids and oil behind. Steam heat is beneficial because it also decarboxylates the cannabinoids and thus THC-A, CBD-A and CBN-A are converted respectively into THC, CBD, and CBN.

A volume of Ethanol (e.g., 100% Ethanol) sufficient to dissolve and extract the oils is added to the steam-dried product, and the combination is vigorously blended and subjected to microwave assisted extraction so as to extract all the biological material. The extracted material is then vacuum filtered through one or more filters including a charcoal filter that retains plant debris, adsorbs the plant pigments in the ethanol and allows the ethanol solvent containing the phytochemicals to flow through so that the filtrate contains all the extracted phytochemicals.

The ethanol-oil from the filtrate is subjected to super critical fluid $CO_2$ extraction so as to respectively obtain at least one of clean, uncontaminated *Cannabis* oil, turmeric oil and ginseng oil, depending on which plants were selected to be included in the process. For example, *Cannabis sativa* is useful for obtaining *Cannabis* oil, *Curcuma longa* is useful for obtaining turmeric oil and *Boswellia serrata* are good sources of frankincense resin oil. Various sub-species, varieties, hybrids, bio-types, and eco-types of the example plants are useful in different example embodiments of the disclosed method.

While example plants and oils are mentioned above, the disclosed can also be potentially applied to the extraction of ethno pharmaceuticals from other medicinal plants.

The obtained, respective oils can be analyzed for content by gas and gas-mass spectrometric analysis in an example embodiment.

According to one example embodiment, $CO_2$ purified oils can be further purified into their respective components by vacuum distillation and or preparative column chromatography.

Embodiments of the present disclosure include combining and blending the oils from *Cannabis sativa*, *Curcuma longa* and *Boswellia serrata* in a massage oil or cream. The composition may be realized as an oil or cream formulation that can reduce pain, relieve inflammation, restore joint flexibility and improve skin health when the oil or cream (e.g., a face cream) is applied topically by massage or rubbing.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method of treating a medical issue, comprising:
   applying a composition to a skin area corresponding to a location afflicted with the medical issue;
   wherein the composition comprises a blend of Cannabidiol (CBD) oil, Cannabinol (CBN) oil, curcumin from turmeric, Boswellic acid, and polycyclic terpenes from *Boswellia serrata*; and
   wherein the medical issue comprises at least one of osteoarthritis, joint pain associated with natural causes or injury, reduced joint function and flexibility after injury or other causes, and photo-aging.

2. The method of claim 1, comprising, prior to said applying:
   blending the CBD oil, CBN oil, Boswellic acid, and polycyclic terpenes in different proportions in the composition with at least one of coconut oil, olive oil, or hemp oil.

3. The method of claim 2, comprising, prior to said applying:
   diluting the CBD oil, CBN oil, Boswellic acid, and polycyclic terpenes in the composition.

4. The method of claim 1, wherein said applying comprises applying the composition to an area of skin compromised due to photo-aging.

5. The method of claim 1, further comprising preparing the composition, said preparing comprising:
   freezing plant parts of *Cannabis sativa, Curcuma longa,* and *Boswellia* serrate;
   reducing the frozen plant parts to a plant powder;
   suspending the plant powder in an aqueous buffer;
   incubating the aqueous buffer containing the suspended plant powder;
   evaporating an aqueous phase of the incubated aqueous buffer through steam heating to obtain a steam dried product; and
   extracting phytochemical oil from the steam dried product, the phytochemical oil including at least the CBD oil and the CBN oil.

6. The method of claim 5, wherein said incubating is performed with at least one pectinase, at least one cellulose, and at least one protease.

7. The method of claim 5, comprising, prior to said freezing:

sanitizing the plant parts, the sanitizing including at least one of washing, ultraviolet irradiation, and ozonolysis.

8. The method of claim 5, wherein said reducing the frozen plant parts to a plant powder comprises pulverizing the frozen plant parts.

9. The method of claim 5, wherein:
   said freezing comprises cooling the plant parts with dry ice; and
   said reducing is performed while the plant parts are being cooled by the dry ice.

10. The method of claim 5, wherein said incubating is performed at approximately 37° Celsius, and is performed for 1-24 hours depending on an amount of the plant powder in the aqueous buffer.

11. The method of claim 5, comprising shaking the aqueous solution containing the powder during said suspending to distribute the contents of the aqueous buffer, thereby digesting cell walls of said plant parts, and releasing contents of the plant parts previously contained by the cell walls into the aqueous buffer.

12. The method of claim 5, wherein said evaporating comprises decarboxylating the suspended plant powder.

13. The method of claim 5, wherein said extracting phytochemical oil comprises:
   dissolving the steam dried product in ethanol; and
   blending the ethanol solution that includes the dissolved steam dried product.

14. The method of claim 1, further comprising purifying at least the CBD and CBN oils through at least one of vacuum distillation and preparative high pressure liquid chromatography (HPLC).

15. The method of claim 14, wherein said purifying is also performed on the curcumin and Boswellic acid.

16. The method of claim 14, wherein the purifying also includes performing super critical fluid $CO_2$ extraction.

17. The method of claim 16, wherein the purifying also includes using preparative column chromatography.

18. The method of claim 17, wherein the preparative column chromatography comprises high pressure liquid column chromatography.

19. A method of treating osteoarthritis, joint pain associated with natural causes or injury, reduced joint function and flexibility after injury or other causes, and photoaging, comprising:
   applying a composition as a face cream, the composition comprising a blend of Cannabidiol (CBD) oil, Cannabinol (CBN) oil, curcumin from turmeric, Boswellic acid, and polycyclic terpenes from *Boswellia serrata*.

20. A composition comprising a blend of pure Cannabidiol (CBD) oil, and Cannabinol (CBN) oil, curcumin from turmeric, Boswellic acid, and polycyclic terpenes from *Boswellia serrata*.

* * * * *